(12) United States Patent
Dwight et al.

(10) Patent No.: US 7,450,227 B2
(45) Date of Patent: Nov. 11, 2008

(54) SURFACE ENHANCED RAMAN SPECTROSCOPY (SERS) SUBSTRATES EXHIBITING UNIFORM HIGH ENHANCEMENT AND STABILITY

(75) Inventors: David W. Dwight, Roalsburg, PA (US); David L. Allara, State College, PA (US)

(73) Assignee: The Penn State Research Foundation, University Park, PA (US)

( * ) Notice: Subject to any disclaimer, the term of this patent is extended or adjusted under 35 U.S.C. 154(b) by 264 days.

(21) Appl. No.: 11/231,177

(22) Filed: Sep. 20, 2005

(65) Prior Publication Data

US 2006/0061762 A1    Mar. 23, 2006

Related U.S. Application Data

(60) Provisional application No. 60/612,291, filed on Sep. 22, 2004.

(51) Int. Cl.
*G01J 3/44* (2006.01)
*G01J 3/00* (2006.01)

(52) U.S. Cl. .................................. 356/301; 356/300
(58) Field of Classification Search ............ 356/301; 359/327, 334; 372/3
See application file for complete search history.

(56) References Cited

U.S. PATENT DOCUMENTS

| | | | |
|---|---|---|---|
| 4,977,038 A | 12/1990 | Sieradzki et al. | |
| 5,255,067 A * | 10/1993 | Carrabba et al. | 356/301 |
| 6,136,704 A * | 10/2000 | Maya | 438/680 |
| 6,203,925 B1 | 3/2001 | Attard et al. | |
| 6,406,777 B1 | 6/2002 | Boss | |
| 6,602,802 B2 * | 8/2003 | Aoi | 438/778 |
| 6,614,523 B1 | 9/2003 | Boss | |
| 6,781,690 B2 | 8/2004 | Armstrong et al. | |
| 6,838,121 B2 | 1/2005 | Weimer | |
| 6,850,323 B2 | 2/2005 | Anderson | |
| 6,873,052 B2 * | 3/2005 | Aoi | 257/760 |
| 6,989,897 B2 * | 1/2006 | Chan et al. | 356/301 |
| 2002/0015150 A1 | 2/2002 | Armstrong et al. | |
| 2002/0105641 A1 | 8/2002 | Anderson | |
| 2003/0026900 A1 | 2/2003 | Weimer | |
| 2003/0175472 A1 * | 9/2003 | Den et al. | 428/66.6 |
| 2004/0096981 A1 | 5/2004 | Weimer | |
| 2004/0150818 A1 | 8/2004 | Armstrong et al. | |
| 2007/0153267 A1 * | 7/2007 | Wang et al. | 356/301 |

OTHER PUBLICATIONS

Futamata, M.; Maruyamab, Y., Ishikawab, M., "Microscopic morphology and SERS activity of Ag colloidal particles,"Vibrational Spectroscopy, vol. 30, Issue 1, Sep. 18, 2002, pp. 17-23.

(Continued)

*Primary Examiner*—Gregory J. Toatley, Jr.
*Assistant Examiner*—Jarreas C Underwood
(74) *Attorney, Agent, or Firm*—Gifford, Krass, Sprinkle, Anderson & Citkowski, P.C.

(57) ABSTRACT

An improved substrate for Raman spectroscopy of an analyte comprises a porous metal film. Enhancement factors and uniformity of the substrate can be enhanced by electrochemical roughening of the film. Improved sensors and spectrometers using such substrates are also described.

20 Claims, 11 Drawing Sheets

OTHER PUBLICATIONS

Xu, H., Aizpurua, J., Kall, M., Apell, P., "Electromagnetic contributions to single-molecule sensitivity in surface-enhanced Raman scattering," Phys Rev E Stat Plasmas Fluids Relat Interdiscip Topics, Sep. 2000, 62(3Pt B): pp. 4318-.

Gunnarsson, L., Bjerneld, E.J., Xu, H., Petronis, S., Kasemo, B., Kall, M., "Interparticle coupling effects in nanofabricated substrates for surface-enhanced Raman scattering," Applied Physics Letters, vol. 78, Issue 6, Feb. 5, 2001, pp. 802-804.

Vo-Dinh, T., Stokes, D.L., "Surface-enhanced Raman detection of chemical vaports with the use of personal dosimeters," Field Analytical Chemistry and Technology, vol. 3, Issue 6, pp. 346-356.

* cited by examiner

ACID ETCHING

Electrochemical Cell

SURFACE ENHANCED RAMAN SPECTROSCOPY (SERS) SUBSTRATES EXHIBITING UNIFORM HIGH ENHANCEMENT AND STABILITY

REFERENCE TO RELATED APPLICATION

This application claims priority of U.S. Provisional Patent Application Ser. No. 60/612,291, filed Sep. 22, 2004, the entire content of which is incorporated herein by reference.

GOVERNMENT SUPPORT

This invention was made with Government support under Contract No. N00014-03-1-0226, awarded by The Office of Naval Research and Contract No. M-67004-99-D-0037 D077, awarded by the United States Marine Corps. The Government has certain rights in the invention.

FIELD OF THE INVENTION

The invention relates to substrates, in particular to porous metal substrates, useful for analytical techniques such as surface enhanced Raman spectroscopy (SERS).

BACKGROUND OF THE INVENTION

In 1974, it was discovered that the Raman scattering signal of certain compounds could be enhanced by orders of magnitude proximate to metallic surfaces roughened on the scale of tens to hundreds of nanometers, a technique called Surface Enhanced Raman Spectroscopy (SERS).

When laser light scatters from a metal surface, typically one photon in a million interacts with the vibrational states of molecules adsorbed on the surface, and the frequency of the scattered photon is shifted accordingly. Averaged over time, the sum of the shifted photon frequencies (the Raman shift) is a vibrational spectrum of the adsorbed molecule. Because every molecule has its own unique fingerprint spectrum, in principle, the SERS response can identify of any chemical of interest.

A conventional SERS substrate prepared by electrochemical roughening yields a random pattern that happens to include some "hot spots" where surface plasmons resonate with the incident radiation—a phenomenon known as Surface Plasmon Resonance (SPR). Analyte molecules in this enhanced electromagnetic field are subjected to stronger polarizing effects and thereby support Raman scattering with higher efficiency. Experiments demonstrating SERS enhancement factors under conditions that were controlled to eliminate the possibility of direct contact between analyte and substrate have lent credence to this concept of electromagnetic enhancement, and based on those experiments and theoretical calculations the SPR is considered to account for the larger component of the SERS enhancement factor, typically of the order of $10^3$ to $10^6$.

A second effect, called chemical enhancement, has been suggested for molecules that become adsorbed onto the surface—thereby coupling the molecule's valence electron charge density with the substrate. This gives rise to extra bound energy states and presents a greater opportunity for energy coupling with the incident radiation. This mechanism is not as well established, but is supported by experiments demonstrating enhancement on the order of $10^1$ to $10^3$ from an analyte adsorbed onto an atomically smooth gold substrate.

Surface Enhanced Raman Spectroscopy (SERS) has the potential to detect minute quantities of organic compounds. The vibrational spectra obtained are unique fingerprints of chemical composition and bonding, thus providing excellent selectivity. SERS typically uses a rough solid surfaces as a substrate upon which molecules are adsorbed, either from solution or the vapor phase. However, laboratory substrate preparations are poor in terms of reproducibility, and typically the enhancement factors vary by orders of magnitude from point-to-point across a given substrate.

Thus there is a need for a process to make SERS substrates that exhibit high enhancement factors which are uniform across the surface, are stable when exposed to environmental conditions over long periods of time, and can be manufactured with a high degree of reproducibility. At present, SERS systems have seen little use in practical, field-portable chemical sensor systems, primarily due to poor reproducibility of SERS-active substrates.

Over the past 25 years, the general approach to preparing these surfaces has been empirical, with laboratory processes developed to produce surfaces for SERS spectra of analytes of interest. Historically, the first SERS-active substrates were electrochemically-roughened silver electrodes, which strongly enhanced the Raman spectrum of pyridine dissolved in water. Colloidal gold and silver particles suspended in a solvent containing certain analytes have also been used as SERS substrates.

However, conventional substrate preparation methods preparations are notoriously irreproducible. Thus, improved methods of manufacturing environmentally stable, sensitive, and reproducible SERS substrates are urgently needed.

U.S. Pat. No. 4,977,038 to Sieradzki et al. describes an electrochemical method of preparing micro- and nano-porous metallic structures. U.S. Pat. No. 6,203,925 to Attard et al. describes methods of preparing an ordered porous metal through an intermediate liquid crystalline phase. However, there is no suggestion in these patents to use metallic structures in any analytical technique.

SUMMARY OF THE INVENTION

Methods according to embodiments of the present invention allow preparation of substrates showing high values of SERS enhancement factors, that are robust, can be cleaned and reused, and which show a high degree of uniformity.

An example method for preparing a substrate for surface enhanced Raman spectroscopy (SERS) comprises depositing an alloy film, the alloy including at least a first metal and a second metal, and removing most or substantially all of the second metal to obtain a porous metal film. The porous metal film can then be used as a SERS substrate. For example, acid etching of a gold-silver alloy film removes the silver component of the alloy leaving a porous gold film. The alloy film has a film thickness, which is preferably less than 1 micron, for example less than approximately 500 nm, such as between approximately 300 nm and approximately 500 nm. The alloy film may be sputter deposited on a support member such as a silicon wafer, and the alloy film and the porous film prepared from it may have columnar structures. Alloy films can be deposited by other techniques, such as thermal evaporation, or electron beam deposition.

Electrochemical roughening of the porous metal film allows higher enhancement factors to be obtained. The enhancement factor for SERS of an analyte arises from interactions between the substrate and the analyte, such as electronic interactions.

In further embodiments of the present invention, a method for enhanced detection of an analyte comprises preparing a textured metal film, for example a porous metal film, lithographed patterned film, or other deposited film, and then further roughening the textured metal film to provide a substrate for the analyte. The further roughening can give greater values of enhancement factors for SERS of the analyte on the substrate. In representative examples, the textured metal film is a porous metal film, and electrochemical roughening the porous metal film gives improved substrates for SERS.

An apparatus for detecting an analyte, such as a SERS spectrometer, comprises a substrate according to an embodiment of the present invention, a radiation source such as a laser providing incident radiation on the substrate, and a detector positioned to receive scattered radiation from the analyte when the analyte is adsorbed on the porous metal substrate. The substrate may be a porous metal substrate, such as a porous gold substrate. A structure, such as a rotating carousel or cartridge, supporting a plurality of substrates may be used to replace the substrate used for detection of the analyte.

DETAILED DESCRIPTION OF THE INVENTION

Figure 1:
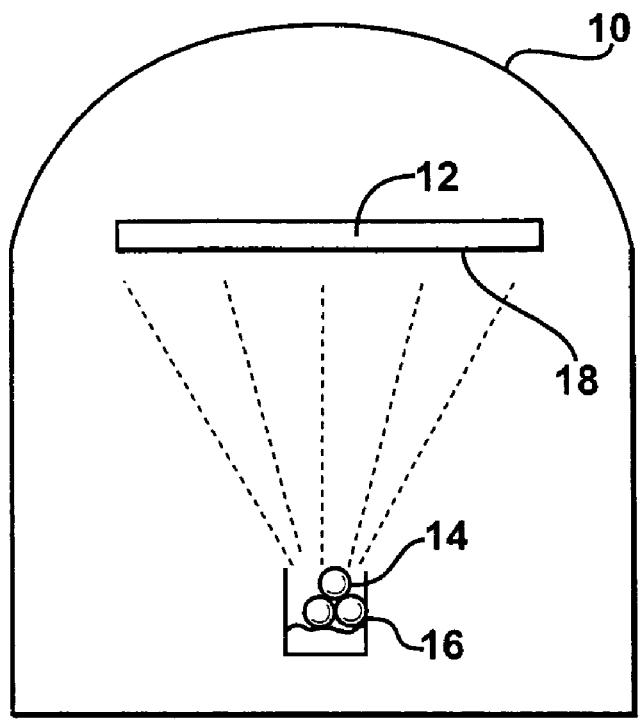
FIG. 1 shows a schematic diagram of a thermal evaporation process used to apply a very thin chromium adhesion layer followed by a gold film on silicon substrates.

Improved substrates for SERS are described, along with improved methods for making SERS substrates. For example, a method for preparing a SERS substrate comprises depositing an alloy of a first metal and a second metal, and removing substantially all of the second metal so as to obtain a porous film of the first metal. In representative examples, the first metal was gold and the second metal was silver, the silver being dissolved by acid etching of the alloy film to leave a porous gold film which had excellent SERS enhancement properties. Gold substrates also have excellent environmental durability and can be cleaned using a UV/ozone treatment. However, other alloy films may be used, and other porous metal films prepared.

The enhancement factor of textured metal films may be further increased by electrochemical roughening. Textured metal films include lithographically patterned films, porous metal films prepared by acid etching of alloy films, colloidal films, and films deposited by chemical vapor deposition, physical vapor deposition, glancing angle deposition, and electrodeposition. Hence, an improved SERS substrate comprises an electrochemically roughened textured metal film, the textured metal film having been first prepared by a non-electrochemical method.

An improved Raman spectrometer comprises a substrate according to an embodiment of the present invention, a radiation source such as a laser providing radiation incident on the porous metal substrate; and a detector positioned to receive Raman scattered radiation by an analyte on the substrate. The substrate may be a porous metal substrate comprising gold, silver, platinum, or other metal. The substrate may be enclosed in a housing having optics (such as a window) to allow incident radiation and scattered radiation to pass through. An inlet port and exhaust for a fluid containing the analyte of interest may also be provided. For example, the analyte can be introduced to the substrate using a gas stream passing through or over the substrate.

Porous gold substrates were prepared and used as substrates for SERS spectroscopy of analytes. Self-assembled mono-layers (SAMs) of para-nitrobenzene thiol (PNBT) deposited from dilute ethanol solutions were used as calibration molecules for determining the relative enhancement factors of the different substrates.

Porous metal substrates can be prepared by a multi-step process. First, an alloy, comprising two or more components, is deposited on a support member, for example by ion-beam sputtering deposition. A metal component of the alloy then is etched away. For example, an acid which dissolves only one of the metal components of an alloy can be used to etch away that metal, leaving behind a porous layer comprising the insoluble metal(s). In one example, a 70% silver/30% gold alloy target was bombarded with a beam of argon ions, resulting in the deposition of a thin film of 70% Ag/30% Au alloy on the support member. The assembly was placed in nitric acid for a certain etching time, allowing most or substantially all of the silver to be dissolved out of the thin film, leaving behind a porous gold film on the support member. In other embodiments, only a top portion of an alloy film is etched, giving a porous metal film formed on an unetched alloy layer.

Preparation of Substrates

Acid etching of the silver components out of a gold-silver alloy film leaves a porous gold film that provides SERS enhancement. Further, electrochemical roughening (also referred to as the Echem process) of a gold film also provided SERS enhancement. However, larger SERS enhancement factors were obtained by electrochemical roughening of porous gold substrates, for example as formed by acid etching, compared to either of those two processes practiced independently. The substrates had much better SERS uniformity than conventional substrates, showing point to point variations having a standard deviation of only ~±15%. In contrast, conventional substrates typically show point to point variations of 200%-200,000%. Porous gold films include acid-etched gold alloy films and other porous gold films.

The examples below describe the formation of improved substrates according to embodiments of the present invention. Firstly, a gold-alloy film is formed using a deposition process, such as sputtering. The film may be converted into a porous gold film by acid etching, or an electrochemically roughened film by electrochemical etching. However, better results were obtained by electrochemical roughening of a porous gold film.

Gold Alloy Film Deposition

Gold alloy films were deposited using sputter deposition methods, as illustrated in FIG. 1. A silicon wafer 12 was placed in a vacuum chamber 10, and a 1-20 nm thick adhesion layer of chromium was thermally evaporated onto the wafer. Next, a ~25 nm thick layer of gold was thermally evaporated on top of the chromium layer. The chromium/gold multilayer is shown at 18. The gold layer is preferably sufficiently thick to have a uniform electrical conductivity. At this stage, the product can be called a flat gold substrate.

Next, a 70% silver-30% gold alloy layer was deposited on top of the gold layer by sputtering a thick, solid layer of the same alloy composition using a directed argon ion beam from an ion gun. This 70 Ag-30 Au layer could be of any thickness greater than a complete monolayer, but is preferably less than approximately 250 nm, such as in the range 25 nm to 250 nm, and more preferably approximately 150 nm to approximately 300 nm. Other deposition methods can be used to deposit the alloy layer, such as evaporation or electron beam deposition.

Figure 2:
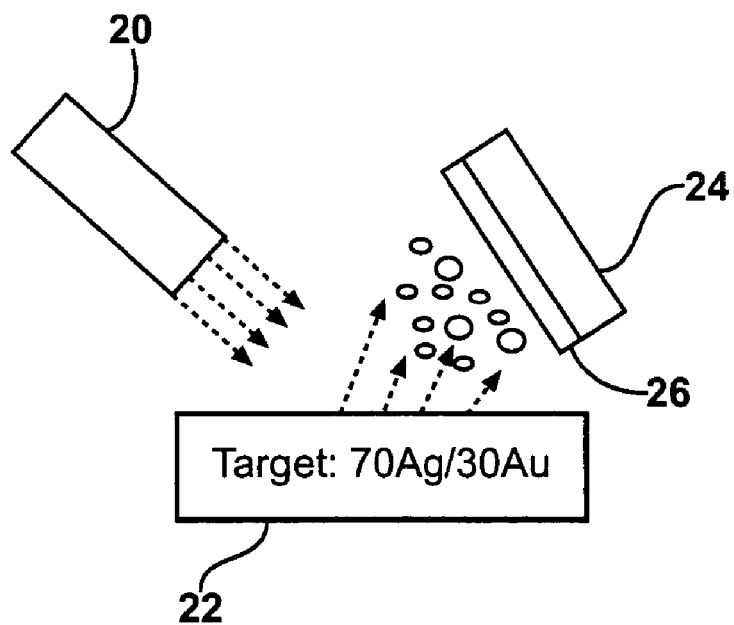
FIG. 2 shows ion-beam sputter deposition of silver/gold alloy films on a chromium/gold coated silicon wafer for making porous gold substrates.

FIG. 2 illustrates a sputtering arrangement, comprising a vacuum chamber 10 fitted with an argon ion gun 20 generating an argon ion beam incident on target 22 (in this example 70 Ag/30 Au). An alloy film 26 forms on the surface 24. Several wafers with nominal alloy film thicknesses typically from 50 nm to 400 nm were prepared by this sputtering method. Other deposition methods, such as thermal evaporation or electron beam deposition, can also be used to deposit the alloy layer.

Formation of Porous Gold Films Using Acid Etching

A silicon wafer supporting a gold alloy film, in a multilayer structure comprising Si/Cr/Au/(70 Ag-30 Au), was prepared by sputtering as described above. After preparation of the gold alloy films, porous gold substrates were prepared by etching away the silver content of the gold-silver alloy film. In acid etching, the gold alloy films were submerged in nitric acid for various times in order to produce a homologous porous gold series with pore sizes varying from 10 nm to 100 nm.

Figure 3:
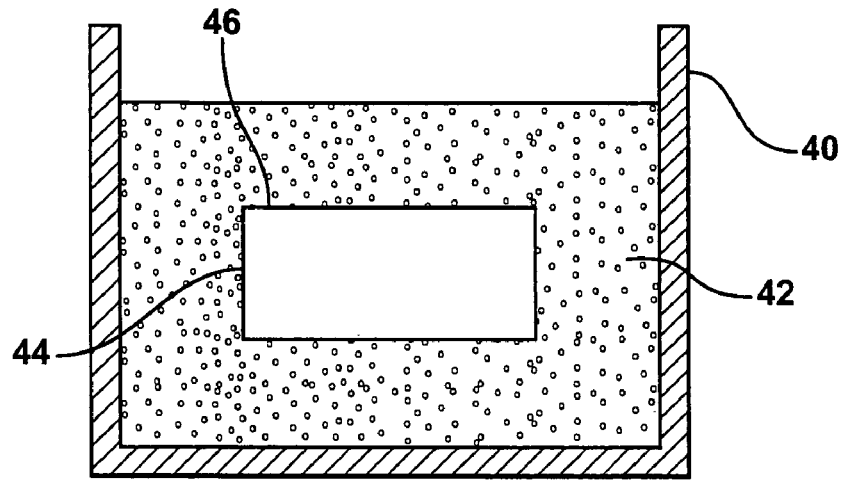
FIG. 3 shows leaching of silver from a gold-silver alloy thin film by submerging the wafer in nitric acid, leaving behind a porous gold film.

FIG. 3 shows the multilayer film 46 supported on silicon 44 placed in a concentrated nitric acid solution 42 held in bath 40. Concentrated nitric acid (70%) was used for faster etching times, but a lower concentration of acid can also be used. After a time period long enough to ensure the removal of as much of the silver as possible, the multilayer-coated silicon wafer was removed from the nitric acid solution acid, rinsed thoroughly with distilled or deionized water, and allowed to dry.

In other embodiments of the present invention, silver is only removed from a surface region of the alloy film. For example, an alloy film may have a thickness of over 100 nm, such as ~200 nm, and silver is only removed from a surface etched layer having a thickness less than 100 nm, such as ~10 nm. A weak acid solution and/or shorter etching time can be used. The unetched alloy film then acts as a support surface for a porous gold film formed within the surface etched layer. In other embodiments, most or substantially all of the silver is removed from the alloy layer.

The exact time of immersion in the nitric acid solution depends upon the solution concentration, the thickness of the alloy layer and the desired average pore size of the final porous gold layer. Typically, the immersion times range from 10 minutes to 30 hours. Naturally it takes longer to remove the silver from thicker alloy layers. At the point in etching time when the silver concentration has been reduced to the minimum observable by x-ray photoelectron spectroscopy, it was found that the resulting pore size is related to the original alloy thickness; the thicker the alloy layer, the larger the pores. Therefore it is possible to make porous gold films with different pore sizes.

Hence, a novel method of preparing a thin gold film having controllable pore sizes comprises providing a gold alloy film having a thickness less than 1 micron, such as a thickness less than 300 nm, and then immersing the film for a predetermined time in an appropriate acid so as to etch the non-gold component. The pore size is related with the film thickness and the etch time. As etch time increases, the pore size increase.

The SERS enhancement of porous gold film peaked at 150-250 nm film thicknesses, and so the film thickness is preferably approximately within that range. Also, the rate of removal of Ag during the acid etching was lowest at ~250 nm, compared with 50 nm and 500 nm thickness films. Stress cracking of the final porous layer occurred only for a thickness 250 nm and above, which is in the range where, in general, thin films begin to be less influenced by the underlying substrate.

Acid Etching Examples

Preparation of a porous gold substrate: Approx. 200 nm thick 70 Au/30 Ag was sputter-deposited on a Si wafer at 10 nm min$^{-1}$ using Ar$^+$ ions at ~10$^{-5}$ Torr. The film was etched in 70% HNO$_3$ for 6 h. The porous gold substrate was immersed for 24 h in ~1.0 mM ethanol solution of p-nitrobenzene thiol. The substrate was rinsed five times in ethanol, followed by a nitrogen dry. Scanning electron microscopy of the porous gold substrate revealed pores ~100 nm. Other acid concentrations can be used, with etching times longer in weaker acid solutions.

There was some variation of Raman intensity across the surface, and in some cases focusing below the surface enhanced the spectrum. SERS spectra showed that 790 nm excitation is more suitable than 532 nm for this gold surface.

High enhancement factors were measured, typically greater than $10^7$. For one substrate, the enhancement factor was $\sim 5.10^7$, with a standard deviation (for point-to-point measurements over a 20 square micron area) of only ±13%. The PNBT signal was relatively uniform over a wide range of regions examined.

Electrochemical Etching (Echem Process)

Figure 4:
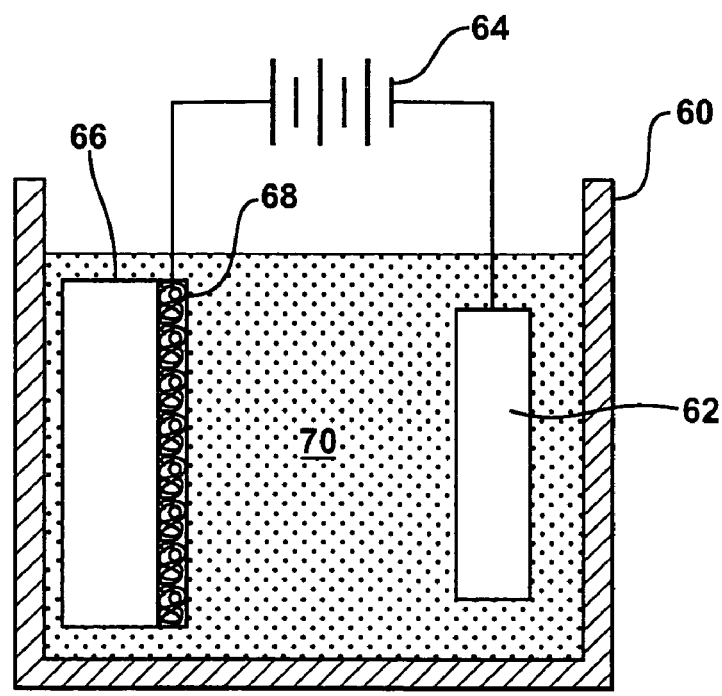
FIG. 4 is a schematic of an electrochemical cell used to roughen flat gold films, or to restructure a porous gold layer, for example through an one or more oxidation-reduction cycles (ORCs)

An electrochemical cell was constructed as illustrated in FIG. 4. A bath 60 contained solution 70, immersing a working electrode 68, the substrate to be electrochemically roughened such as a flat gold substrate or a porous gold substrate. The substrate was supported by a silicon wafer 66. A counter electrode 62 comprised platinum mesh. The reference electrode used (not shown) was Ag/AgCl, and potentials were measured with respect to Ag/AgCl. An electrical potential source 64 provided the electrical potential applied between the sample substrate (working electrode) and the counter electrode.

A typical electrochemical roughening cycle was as follows: the potential was ramped up to 1200 mV in 5 seconds, and then held at 1200 mV for 1 to 30 seconds. Next, the potential was ramped down to −250 mV in 5 seconds, and then held at −250 mV for 20 seconds.

In one approach, a flat gold substrate was prepared. A 2" silicon wafer was coated with ~250 nm of thermally evaporated gold on top of a 6 nm chromium adhesion layer. One half-wafer was submerged in 0.1N KCl solution in a beaker with a platinum counter-electrode and an Ag/AgCl reference electrode, as discussed above in relation to FIG. 4. The number and duration of cycles were varied, using a typical roughening cycle from −0.3 to +1.2V, with respect to Ag/AgCl, using a VoltaLab PGZ100 (Radiometer Analytical, Lyon, France) system to produce various degrees of roughness.

In general, the roughness of the gold electrodes increased as the number of ORC cycles increased. However, in contrast to the literature on thick gold mirror-electrodes, the 100 nm thin films were entirely etched away after 25 cycles. The point of diminishing returns was about 10 cycles.

Gold was chosen as the substrate material, in part, for its resistance to the environment, and its imperviousness to aggressive cleaning methods. However, porous metal SERS substrates can also be prepared using other metals. Porous metal substrates can also be prepared by templating techniques. In the examples below, the electrochemical roughening process (or "Echem" process) was evaluated for flat gold substrates, and for acid-etched porous gold substrates in what is referred to as the Porous/Echem process.

SERS Enhancement Measurements of Acid-Etched Porous Gold Substrates

Figure 5:
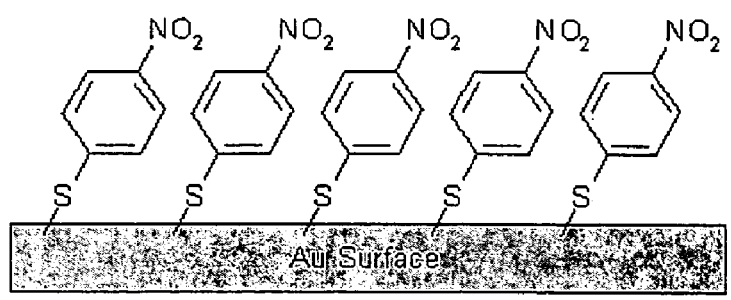
FIG. 5 is an idealized representation of a PNBT SAM (para-nitrobenzene thiol self-assembled monolayer) on a gold surface.

In order to compare the SERS enhancement factors of various gold surfaces, a molecule that is known to form close-packed monolayers on gold was selected. Such a molecule is para-nitrobenzene thiol (PNBT), whose chemical structure and idealized arrangement on a gold surface is shown in FIG. 5.

Based on the literature, which predicts enhancement of electromagnetic field strength to increase rapidly as the distance between conducting elements decreases, we anticipated that SERS intensity would increase for porous gold substrates as the pore size decreased. But experimentally, we found the opposite to be the case.

XPS analysis of some samples showed significant compositional changes on porous gold substrates over time. However, in contrast, SERS enhancements were relatively stable for the same samples. The XPS technique provides data averaged over the whole substrate, whereas the SERS technique provides data related to the properties of the enhancement sites, which may be as little as 1% of the total surface area.

Figure 6:
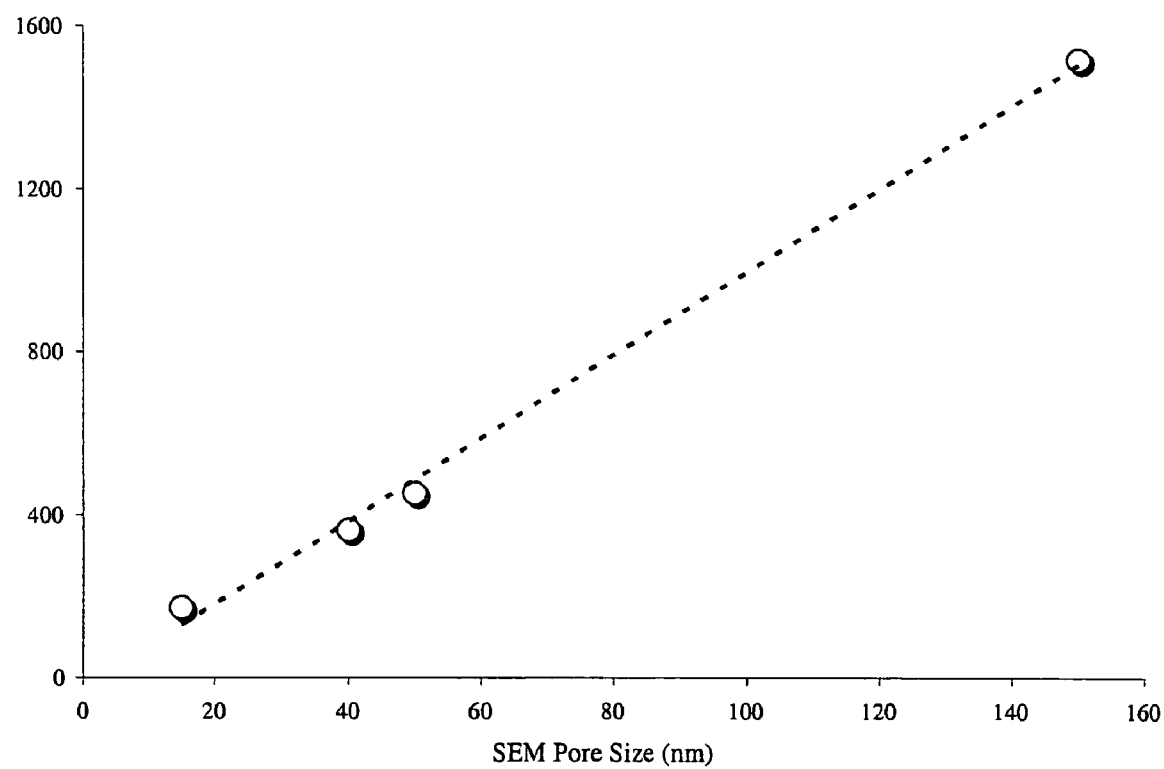
FIG. 6 shows a linear relationship between SERS intensity and pore size as determined by SEM for porous gold substrates.

FIG. 6 shows the trend of relative SERS intensity (in counts per second) for different pore sizes when various porous gold films were prepared according to the protocols above. FIG. 6 illustrates a linear relationship found between SERS intensity and pore size of porous gold SERS substrates. This result is opposite from the theoretical prediction, indicating that unidentified confounding factors are dictating the outcome. There is a direct, linear relationship: as pore size increases, the SERS intensity increases.

The maximum relative SERS intensity is about 1500 counts when the pore size is about 150 nanometers and the minimum is about 200 counts when the pore size is about 10 nanometers. An enhanced value of relative SERS intensity of about 60,000 counts was obtained from both of those samples by subjecting them to an electrochemical roughening process. The 150 nm pore-size sample increased in SERS intensity by a factor of 40 when subjected to one standard ORC. The 10 nm pore-size sample increased in SERS intensity by a factor of 300 when subjected to an electrochemical cycle which used 10 second dwell times instead of the standard 30 seconds.

FESEM was used to collect high-magnification images of the porous gold SERS substrates. The pore- and feature-size and shape depends upon both the thickness of the original alloy thin films, and the time of etching in concentrated nitric acid. This provides a means for structural control in the 10 nm to 100 nm range of sizes.

Figure 7A:
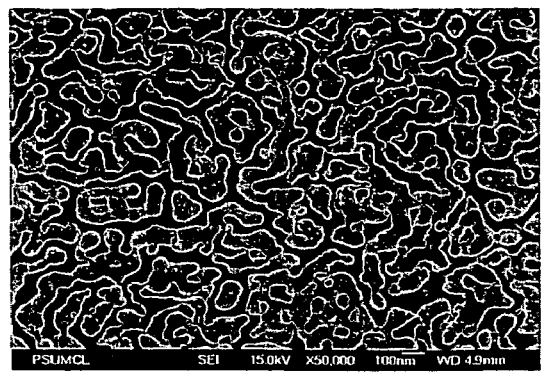
FIGS. 7A-7C show electron micrographs of porous gold substrates.
Figure 7B:
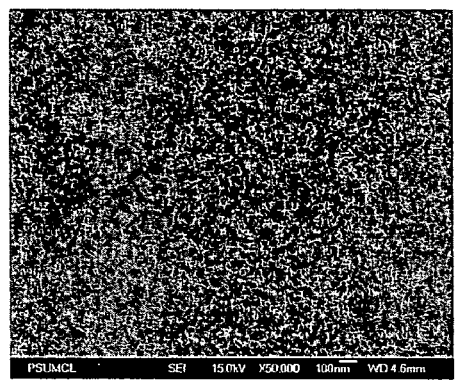
Figure 7C:
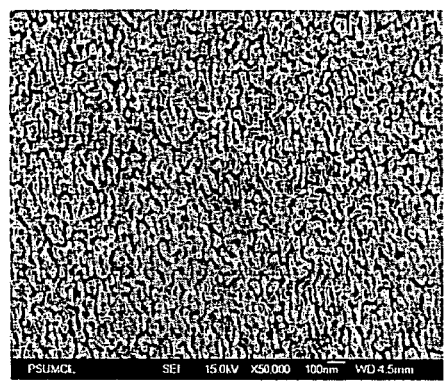

FIGS. 7A-7C show SEM images of typical porous gold SERS substrates with different pore sizes, obtained in this manner. FIG. 7A shows a porous gold substrate formed by submerging a gold-silver alloy film in concentrated $HNO_3$ for >6 hours. The porous gold film has features of approximately 100 nm.

It is readily apparent that features are relatively uniform in each case, and that pore size and shape are similar to the gold ligament size and shape. Because electric field strength increases as the distance between metallic conductors decreases, we used the shorter dimension of the pores as the pore size.

SERS Enhancement of Electrochemically Roughened Substrates

Figure 8:
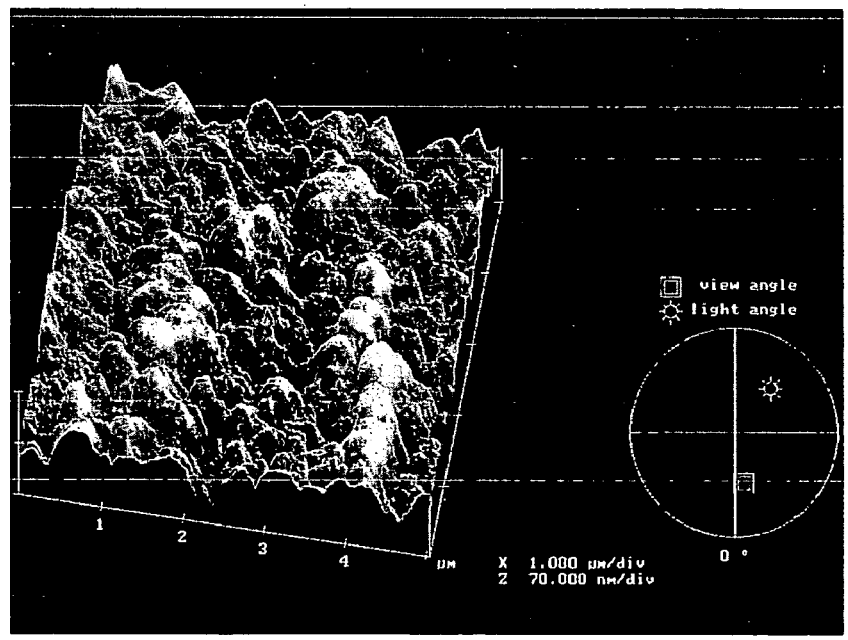
FIG. 8 shows an atomic force microscope image of an electrochemically roughened SERS substrate.

FIG. 8 shows an atomic force microscopy (AFM) view of a typical Echem SERS substrate. The term "Echem" substrate refers electrochemically roughened flat gold layers, whereas a "Porous/Echem" substrate is a porous gold film that has then been electrochemically roughened.

The digital xyz data are integrated over the entire field of view to obtain the root-mean-square (RMS) roughness of that area. The RMS roughness was averaged for five different locations and at two magnifications for many different Echem treatments. We found a linear correlation between the roughness value for 5×5 micrometer areas, but not for 500×500 nanometer areas.

Electrochemical Roughening of Porous Gold

Porous gold substrates prepared by acid etching of a gold-silver alloy film were subject to electrochemical roughening. The resulting substrates had excellent SERS enhancement properties.

Figure 9A:
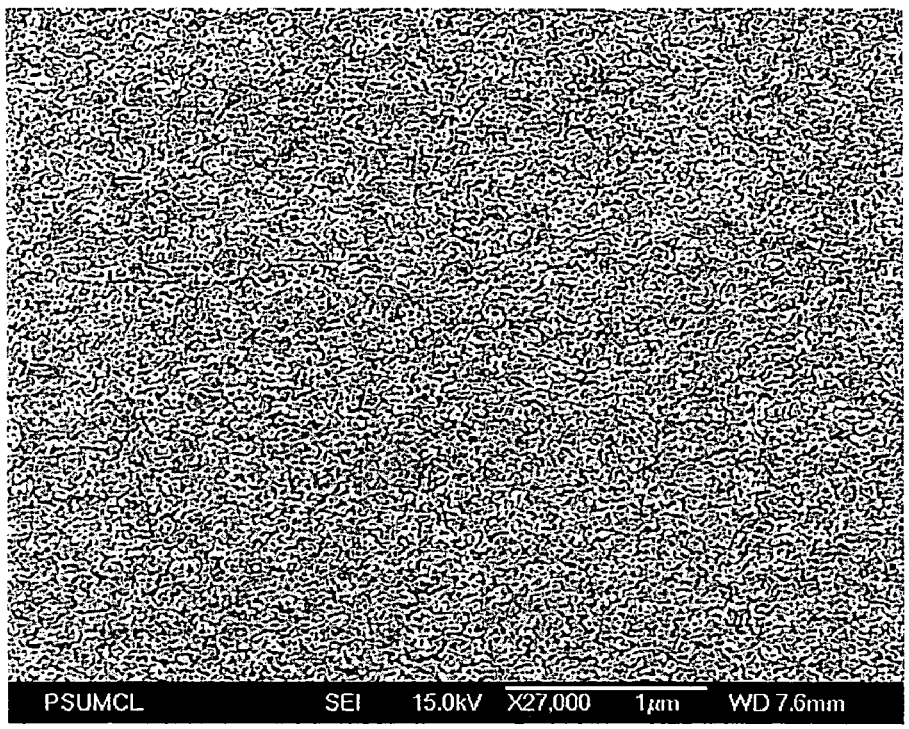
FIG. 9A-9D shows porous gold before and after electrochemical roughening.
Figure 9B:
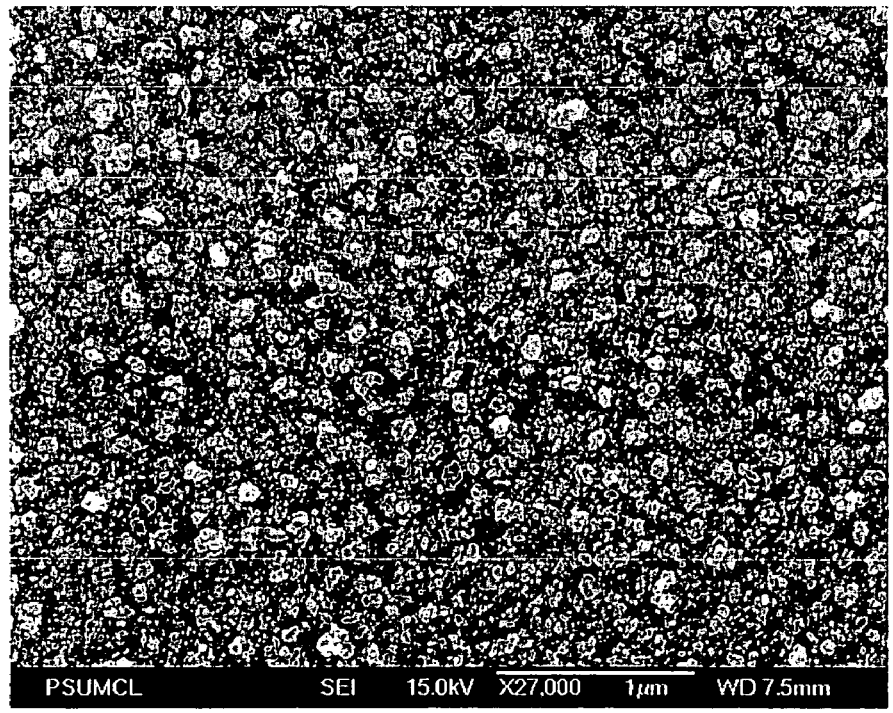
Figure 9C:
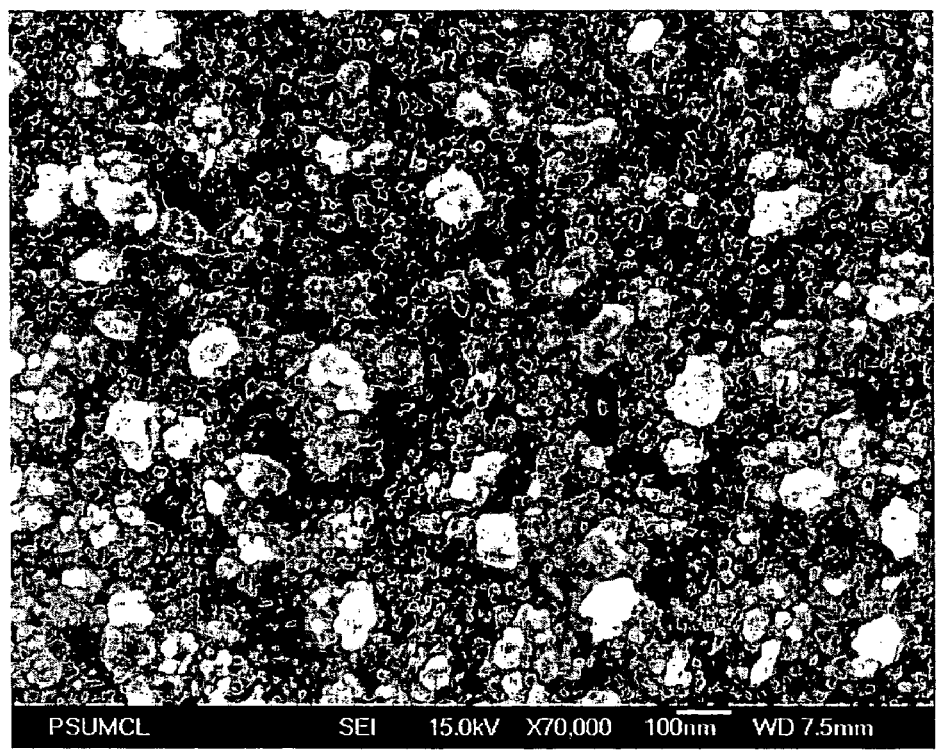

FIG. 9A-9E illustrate the effect of electrochemical roughening on substrate topography. FIG. 9A shows a porous gold substrate. FIGS. 9B and 9C are different magnifications of the same area after electrochemical roughening of the substrate shown in FIG. 9A. The electrochemical roughening appears to chop the ligaments of gold in the porous gold substrate, and redeposit gold as clusters as seen in FIG. 9B. FIG. 9C, at higher magnification, shows fine particulate material between clusters, which probably contribute to "hot spots", areas of high enhancement. A dense array of particles of around 1 nm-10 nm diameter is formed, with the particles closely packed together.

An example approach to forming electrochemically roughened porous gold is as follows. Starting with a wafer with 200 nm nominal thickness of alloy, 6 hours of nitric acid etching produced a typical porous gold substrate. After 5 electrochemical roughening cycles, the topography had changed. As discussed above in relation to FIGS. 9A-9C, the porous gold "ligaments" were seen to be chopped into pieces about 100 nm in size, and those pieces re-aggregated into a new topography that was reminiscent of deposits of colloidal gold particles. It is possible that the "hot spots" are found around the places where particles contact each other. One mechanism for this particular treatment appears to be dissolution and redeposition, as some features in an electrochemically roughened film may be larger that those in the porous gold precursor film.

Figure 9D:
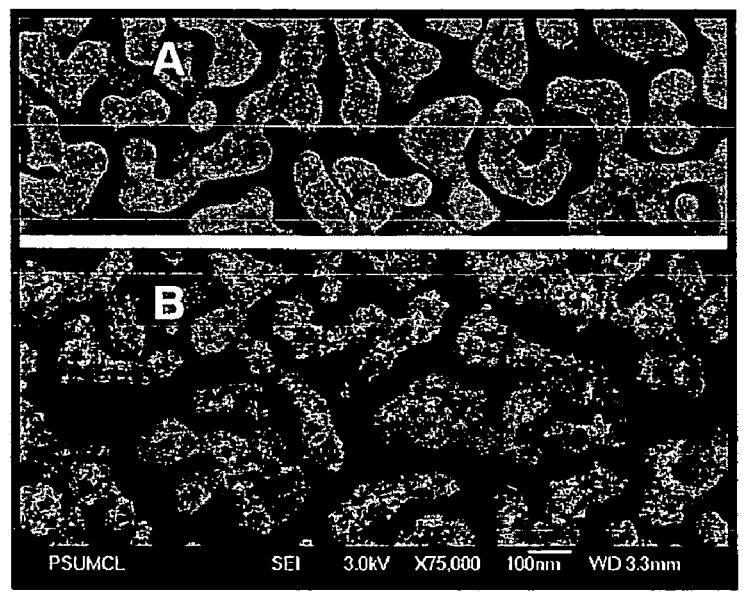

FIG. 9D shows the same porous gold substrate before and after electrochemical roughening. The topography is noticeably different from that seen in FIGS. 9B and 9C. There appears to be a large number of sharp tips and cratering in the surface. The gold tips have dimensions approximately $\leq 10$ nm, and the craters also have nanoscale dimensions.

Figure 10:
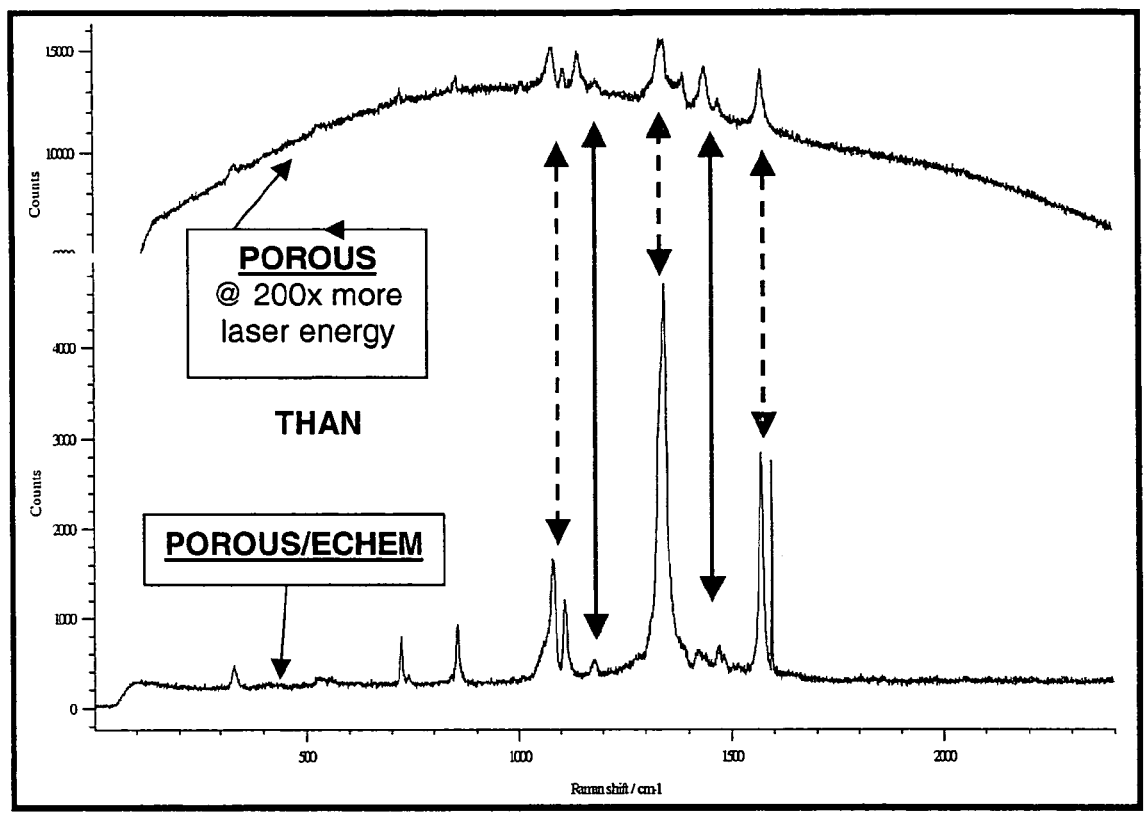
FIG. 10 shows SERS spectra of PNBT on porous gold before [top curve], and after (lower curve) electrochemical roughening.

FIG. 10 shows typical results obtained using a Renishaw MicroRaman spectrometer (Renishaw plc, Wotton-under-Edge, UK). Spectra were collected from both Porous (porous gold prepared by acid etching of an alloy film) and Porous/Echem (electrochemically roughened porous gold) ends of the substrate discussed above in relation to FIG. 9. In order to obtain spectra from the Porous part, laser power and integration time had to be increased by a factor of 200 to make this comparison. Selecting the 1330 cm$^{-1}$ peak (the carbon-nitrogen stretching vibration, at the shortest dashed arrow), there is a factor of about 10 difference in peak area. Thus the Echem treatment increased the SERS enhancement factor by a factor of 2,000.

Figure 11:
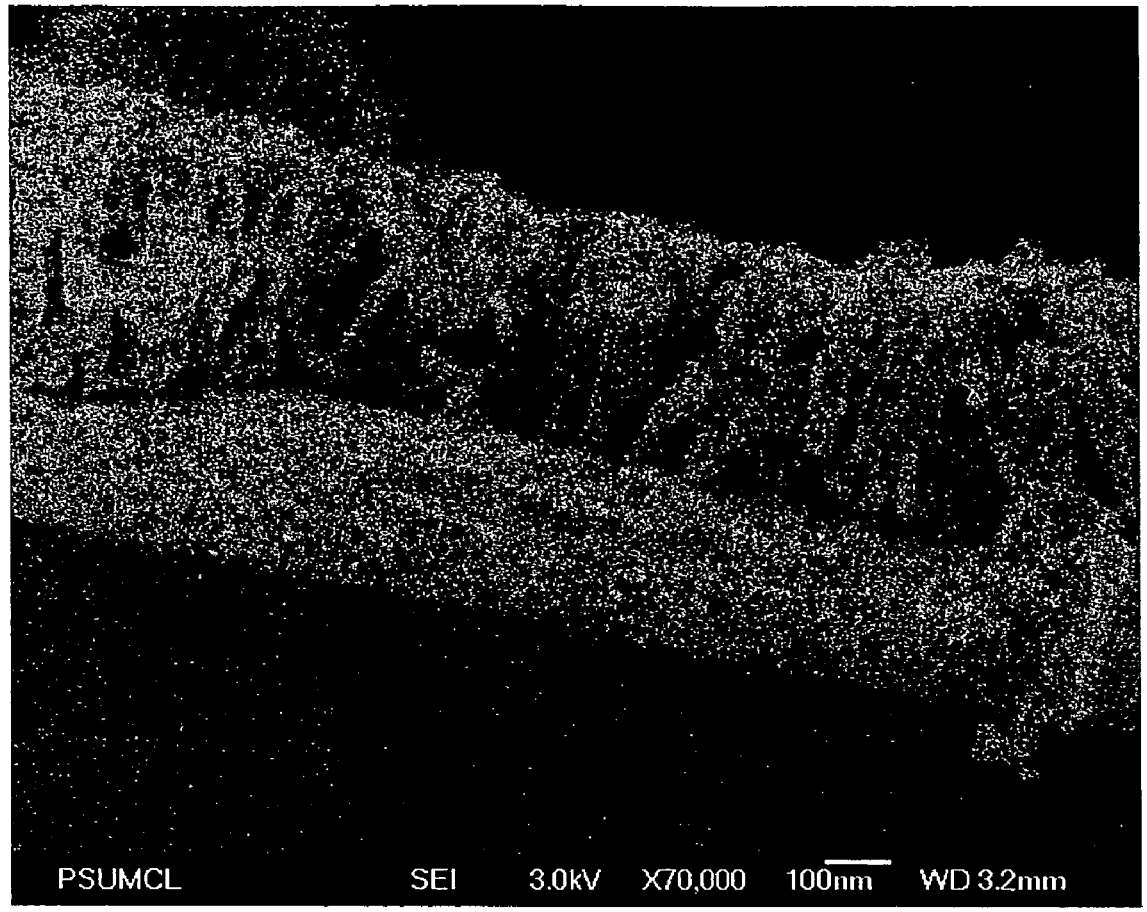
FIG. 11 shows a cross-section of a substrate, illustrating a columnar structure.

The solid (non-dashed) arrows in FIG. 10 indicate how the increase in laser energy caused new peaks to grow in, indicating a decomposition product of PNBT. With more laser power, those peaks grow rapidly to be the most intense peaks in the spectra. FIG. 11 shows a photomicrograph of cross-section of an electrochemically roughened porous gold film. There is a preponderance of columns, oriented perpendicular to the substrate. Possibly, without wishing to be limited by this suggestion, during sputter deposition, the nucleation and growth mechanisms produce columnar growth, and nitric acid penetrates rapidly into the columnar grain boundaries, and etching of the columns proceeds both horizontally and vertically.

For the electrochemical process, SERS intensity was found to be approximately proportional to surface roughness as measured either by AFM or ellipsometry. The feature size characterized by AFM is greater than those responsible for SERS enhancement. However, the possibility that increased roughness reflects the creation of narrow crevices cannot be ruled out. Vapor phase adsorption and SERS detection of aromatic thiols was demonstrated.

Figure 12:
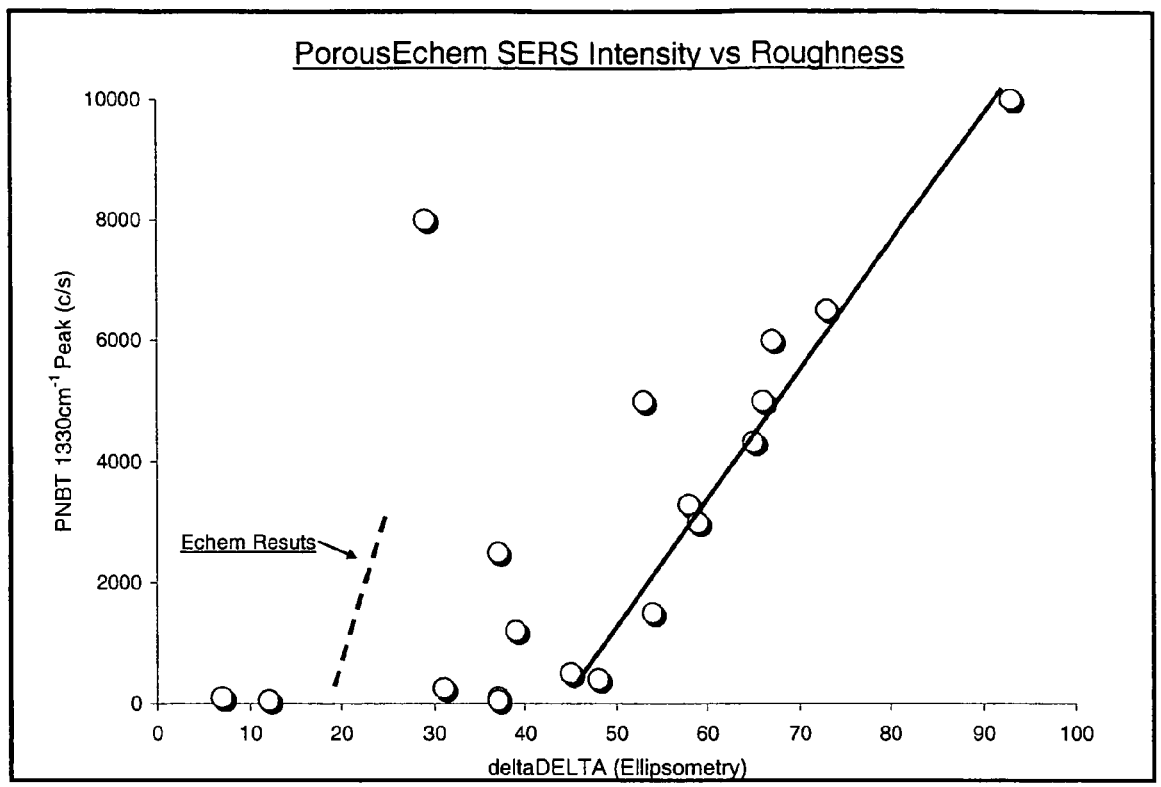
FIG. 12 illustrates the Raman intensity versus roughness for an electrochemically roughened SERS substrate.

FIG. 12 illustrates how the SERS enhancement varies with roughness, as determined by ellipsometry measurements. For electrochemically roughened porous gold (Porous-Echem) substrates, data are shown by circles with a solid line to guide the eye. The SERS enhancement factor was found to be roughly proportional to the change in the value of Delta as measured using ellipsometry, and hence with the surface roughness. Hence, ellipsometry can be used to characterize SERS substrates, for example, for quality control during a manufacturing process. Similarly, the SERS enhancement was correlated with the roughness determined by AFM measurements. The polarized laser light in SERS is apparently interacting with the same surface features that dominate the roughness on the sub-micrometer scale. FIG. 12 also shows as a dashed line typical data for the Echem process alone (electrochemically roughened flat gold substrates).

The term deltaDelta refers to the reduction in Delta with respect to a flat gold film. The Delta value for flat gold is 109°, so a deltaDelta of value of 40 corresponds to a Delta value of 69°. The data were collected for a variety of fabrication conditions, and those points falling well to the left of the line showed different porous gold topographies. This figure shows that ellipsometry is extremely valuable for rapid characterization of the SERS substrates. The SERS enhancement, and hence quality of the substrate, can be rapidly evaluated without having to expose the substrates to an analyte. Hence, high quality and highly reproducible SERS subtrates can be made for the first time. As made substrates can be sorted into batches according to measured ellipsometry values, or other surface roughness parameter value, and supplied to customers along with an accurate prediction of SERS enhancement when used. If the deltaDelta value does not exceed a threshold, such as 40, the sample may be rejected.

The enhancement factor was proportional to the roughness of electrochemically roughened substrates, and inversely proportional to the pore size of porous gold substrates. However, much greater SERS enhancement factors were obtained by electrochemical roughening of porous gold substrates, compared to either of those two processes practiced independently. The SERS enhancement of porous gold films was increased by electrochemical roughening, and the uniformity of the substrate was also increased.

SERS enhancements were fairly uniform over central regions of the prepared substrates. When the substrate was completely immersed within the solution in the electrochemical cell, as shown in FIG. 4, edge effects were observed, apparently due to the distorted potential lines and/or the increased importance of lateral etching near the edges. However, away from the edges, uniformity was excellent. Edge effects were eliminated using a cylindrical cell where only a central circular portion of the substrate was exposed to the solution. De-aeration of the solution, for example by bubbling nitrogen through the solution to remove oxygen, was found to further reduce edge effect. Any electrochemical cell configuration can be used for the electrochemical roughening process.

In a representative example, a porous gold substrate was prepared, one half of the substrate was then electrochemically roughened, followed by SERS of the whole substrate coated with a SAM. The SERS intensity was at least 200 times greater after electrochemical roughening. The intensity was very uniform within the central region. Data were collected within a 20×20 micron 'grid', collecting spectra every micron (a total of 440 spectra), and found that every Raman spectrum was enhanced. The maximum enhancement was only about twice the minimum, and the standard deviation was about +/−15%.

Exemplary relative enhancement factors (EF) for the ~1330/cm line (633 nm laser) of 4-fluorothiophenol (PFBT) SAMs on a porous gold sample were calculated using a ratio with the normal Raman spectra from neat PFBT and benzene in capillary tube using the same Renishaw 50× objective. Using Renishaw software, baselines were subtracted, and then peak intensities (cts/s) were determined from the ratio of peak area (counts) to the integration time(s). An estimate of the lower limit was done by using the diffraction-limit equations obtained for the optics of this instrument from the manufacturer, and the result was EF=8.4×10$^4$. However, the spot size was measured to be 1.0 um in diameter at 50×, where maximum laser power was 2.5 mW. The volume sampled was assumed to be 5 µL. With these assumptions the result is: EF=6.9×10$^5$. By ratio of Raman peak intensity to that of benzene, the PFBT Raman cross-section is S=1.1×10$^{-33}$ m$^2$/molecule per steradian. This value can also be used for calculating EFs.

A SERS spectrum of PNBT on electrochemically roughened porous gold (Porous/Echem) was enhanced by a large factor (1.6×10$^4$) relative to a PNBT SAM on a commercial substrate (Klarite (TM), Southampton, UK). The Klarite enhancement was substantially less than expected based on manufacturers specifications.

Figure 13:
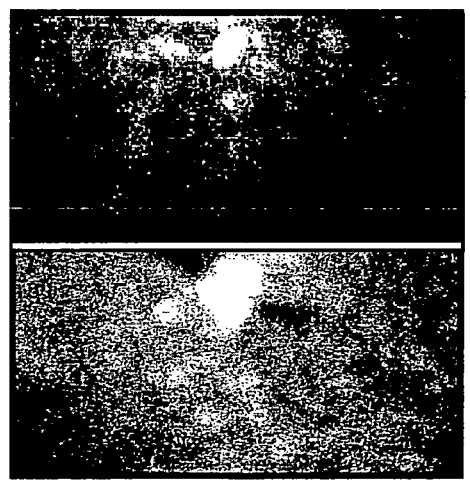
FIG. 13 shows a Raman image of an electrochemically roughened SERS substrate with a monolayer of PNBT.

FIG. 13 shows Raman intensity maps of an electrochemically roughened flat gold substrate (top) versus an electrochemically roughened porous gold substrate (bottom). In the first case, the ratio of brightest to darkest regions was approximately 1000, whereas in the latter case, the ratio was approximately 3. The Raman imaging optics had a tendency to make the center of the field of view brightest, and these images show the lower half of the field of view.

Other Preparation Methods

Other preparation methods can be used to form porous gold substrates, as described in more detail below.

Electron Beam Nanolithography

Figure 14:
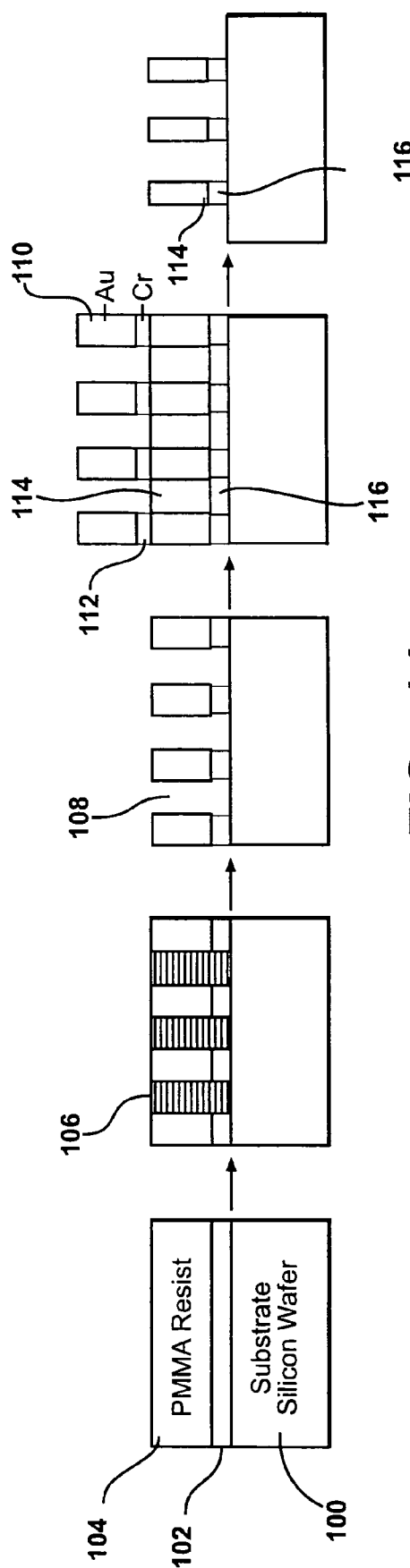
FIG. 14 shows a schematic for nano-fabrication of SERS substrates using electron beam lithography.

FIG. 14 illustrates an example nanofabrication process which can be used to prepare a patterned substrate for use in SERS. The patterned substrate may then be electrochemically roughened.

In an example process, about 100 nm thick of PMMA two-layer resist (layers 104 and 102) was spun onto a silicon wafer 100. A write pattern 106 was formed with an electron beam. The write pattern was removed by development, to provide gaps 108. Vacuum evaporation was used to give a chromium layer (112 on the remaining resist, 116 in the gaps) and a gold layer (110 on the resist, 114 in the gaps). Lift-off of the resist and metal supported thereon left columnar structures of gold 114 on chromium 116, material which earlier formed in the gaps. Nanofabrication using this lift-off technique produced a highly uniform distribution of surface features. For example, a close-spaced pattern of circles was formed in PMMA, giving 55 nm-high Cr/Au posts.

Figure 15:
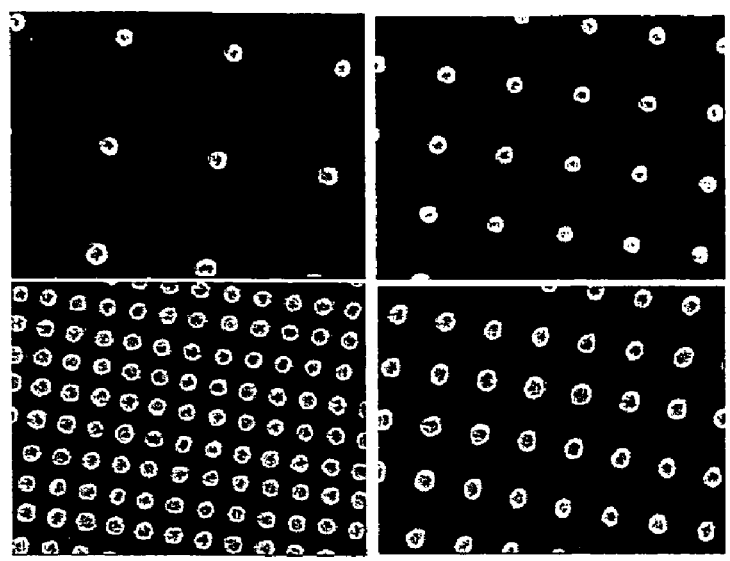
FIG. 15 shows electron micrographs of column patterns nano-fabricated by electron beam nano-lithography.

FIG. 15 shows FESEM views of four typical patterns in which the inter-column distance was changed by integral multiples of the column diameter. Such structures may be useful for micro-Raman applications. Other lithographic techniques, such as optical, WV, or x-ray lithography may be used.

Figure 16:
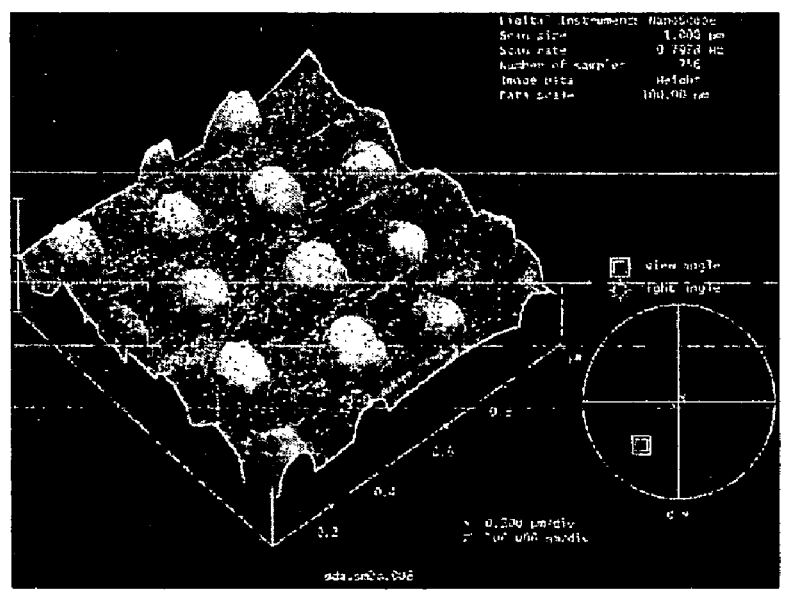
FIG. 16 shows an atomic force microscopy (AFM) image of a column pattern made by electron beam nano-lithography.

FIG. 16 shows an AFM image of a column pattern made by E-beam nano-lithography. The AFM image reveals that the top of each column is not flat, but rather has a tooth-like topography, which might provide more hot spots for SERS enhancement, in addition to those engineered between columns.

Using a Renishaw spectrometer with 50× objective, spectra were collected on four dose-array squares with nominally 100, 150, 250 and 350 nm gaps between 100 nm diameter, 150 nm tall gold 'posts' on silicon. The results show a sharp increase in SERS intensity when the gaps were 100 nm or less. Plotted on a linear scale, the results show that the gap is the major variable. A power-law trend line fitted the data well. Extrapolation to gaps <100 nm indicates gains of 1 order of magnitude at 50 nm, 3 orders at 10 nm and 6 orders at 1 nm. A molecular ruler fabrication approach (e.g. Hatzor and Weiss Science 291, 1019 (2001)) can be used to form these smaller gap dimensions.

Glancing Angle Deposition

SERS substrates comprising rough gold films may also be prepared by glancing angle deposition. For example, a gold film can be prepared using a deposition angle of between 10° and 45°, where 0° corresponds to grazing incidence.

Substrates were prepared in a thermal chamber with the substrates aligned at angles from 10 to 60 degrees to the source, and without rotation during deposition. The coatings show an indication of roughness, the ellipsometric Delta value decreased from 109 (pure gold) to range of approx. 70-100 degrees, i.e. deltaDelta 10-40. The substrates were incubated for 48 hrs. in PFBT. GLAD substrates with high Delta values showed no Raman activity, whereas Delta <70 produced a good PFBT spectrum, similar to that found for porous gold.

Other Deposition Processes

Low temperature physical deposition, for example at a temperature such as 20 K, can also be used to deposit rough gold films. After deposition of such films, electrochemical roughening can be used to further enhance enhancement factors.

A surface may be coated with nanostructures, such as nanowires, which are then subsequently electrochemically roughened.

In other examples, a mixture of colloidal gold and polymer microspheres (e.g. polystyrene microspheres) is deposited on a substrate. Removal of the polymer microspheres using heat and/or solvent treatment leaves a porous gold microstructure, which may be partially sintered. Electrochemical roughening can further enhance the SERS signal. A colloidal suspension comprising a gold/silver alloy can be used, and removal of the silver (as describe above) used to further enhance the SERS signal.

Other patterned substrates that may be electrochemically roughened include porous metals (such as acid-etched alloy films); films prepared by electron, ion beam lithography or other lithography process; nanoparticle or nanotube arrays; colloidal crystals; and films prepared by chemical or physical vapor deposition.

Electron beam, UV, visible, or other form of lithography can be used to prepare patterned substrates. Patterned substrates, such as those described above, may then be subjected to electrochemical roughening to further increase the enhancement factor. In other examples, patterned substrates can be prepared using a combination of lithography and the porous gold preparation method described above. Gold-black substrates can be prepared by electrodeposition, and used for SERS substrates.

A templating method can also be used to fabricate patterned gold substrates. Electron beam lithography is used to form a master, which is then stamped onto the substrate. For example, a replica in silicone rubber can be formed, and the replica used to stamp a high-resolution resist pattern onto a gold substrate. Etching of the exposed gold, followed by resist removal from the remaining gold, gives a patterned gold substrate. The pattern may be nanoscale. Further electrochemical roughening can then be used to increase SERS intensity.

Further Details of Surface Characterization Methods

More details of surface characterization methods used are provided below.

Surface Characterization Using SAMS

Relatively low molecular mass, linear molecules with thiol end groups comprise a class of molecules known as self-assembling monolayers (SAMs). The electronic structure characteristic of the presence of the benzene and nitro-groups in PNBT is known to have a relatively high cross-section for Raman scattering, thus making PNBT easier to detect and quantify in the SERS experiment. It is well known that when gold surfaces are incubated for 24 hours or more in 1 millimolar (mM) solutions of thiols in, e.g., ethanol or tetrahydrofuran, self assembly takes place and chemically bonded monolayers are formed, containing a gold thiolate group. This was the process used to prepare the surfaces analyzed by SERS herein.

Spectral intensities of para-nitrobenzene thiol (PNBT) self-assembled monolayers deposited on the substrates (from solution or vapor-phase) were used to judge sensitivity, and Raman images were collected in order to identify the distribution of hot spots.

Assuming that a monolayer of PNBT covers each substrate uniformly, the area under the two most prominent Raman peaks of PNBT (1550 cm$^{-1}$ and 1370 cm$^{-1}$) was used as a measure of the relative enhancement factor for each substrate.

Hence, the enhancement factor was determined using para-nitrobenzene thiol (PNBT) self-assembled monolayers (SAMs) formed on freshly-prepared SERS substrates by 24-hour incubation in one millimolar PNBT solutions in absolute ethanol. After removal from the PNBT solution, the substrates were copiously rinsed with absolute ethanol, and then blown dry with, and stored under nitrogen in the dark. This procedure produces a single, well-packed monolayer of PNBT, chemically bonded to the substrate through formation of gold thiolate, and the nitrobenzene group has a high Raman cross-section. Methods in the literature for estimating SERS enhancement factors usually rely upon physically adsorbed dye molecules with very high Raman cross-sections such as Rhodamine 6G (Rh6G). No rinsing can be performed on such substrates because all the dye will wash off. Thus, the dye layers are likely to be very non-uniform, and the high enhancement factors reported could be due to agglomerations of dye (i.e. a bulk sample).

Surface Characterization Using Ellipsometry

Ellipsometry was routinely performed with a Gaertner AutoEl-II (Gaertner Scientific Corporation, Skokie, Ill.) after each step in both the electrochemical and the porous processes. The change in the value of Delta was taken to be proportional to surface roughness for the electrochemical process. A Digital Instruments Nanoscope IIIa atomic force microscopy (AFM) was used to obtain 3D views of the substrates at high magnification as well as to quantify surface roughness. Complimentary high magnification images of the SERS substrates were obtained with a JEOL 6700F field emission scanning electron microscope (FE-SEM, JEOL USA, Peabody, Mass.), from which average pore sizes were determined for porous gold substrates. A Kratos Axis 165 Ultra x-ray photoelectron spectrometer (XPS, Kratos Analytical Inc., Chestnut Ridge, N.Y.) was used to determine the chemical composition and bonding of the top 5 nm of the SERS substrates.

For the electrochemically roughened substrates, the SERS enhancement factor was roughly proportional to the change in the value of Delta, and hence with the surface roughness. Hence, ellipsometry may be used to characterize SERS substrates, for example during a manufacturing process.

In an example, solid PNBT was placed 5 cm from a porous gold substrate within a sealed enclosure. A SERS signal, originating from PNBT naturally subliming from the solid, was detectable on the substrate after 30 seconds had elapsed. (SERS spectra were obtained as a function of time, and extrapolation back in time was used to determine the initial detection time).

Physisorbed non-thiol analytes may be selectively detected by coating a SERS substrate with functionalized molecules which interact with the analyte of interest. For example, functionalized thiols may be used, for example Lewis acid functionalized thiols can be used for Lewis basic analytes and vice versa.

Applications

Improved SERS substrates can be used in analytical instruments, for example in a portable Raman spectrometer useful for environmental monitoring. For example, analytes in air, water, smoke, blood, saliva, urine, respiration, exhaust gases, chemical processing, food processing, and the like may be detected. Samples may be removed from a practical surface of interest by sublimation of a solid, evaporation and recondensation, absorption from a vapor stream, or dissolution in a solvent, and deposited on a metal film within the spectrometer.

Spectrometers

An improved Raman spectrometer comprises a laser, a porous metal film, a dispersive element, and an optical detector. The porous metal film is used to support the analyte, and to enhance the Raman scattered signal.

Separation of vapor components within an analyzed gas can be enhanced using an aerosol 'scrubber', which sorbs compatible gases within liquid nanodrops, and an ionizer to give negative charges to the resulting nanodrops. The substrate can be positively charged to precipitate the nanodrops onto the SERS substrate electrostatically. After SERS analysis, the substrate can be cleaned, for example by heating; passing an air flow over the substrate; treatment with UV, ozone, and/or RCA-1; or some combination thereof.

A spectrometer may comprise a substrate according to the present invention housed in an enclosure, the enclosure having a flow-through capability allowing an analyte-containing fluid to pass through or over the substrate. In a flow-over mode, air is passed through the enclosure and over the substrate. In a flow through mode, air is passed through the porous SERS substrate (which may be mounted on a porous glass frit or other porous support). The air entering the enclosure may be passed first through an aerosol module and/or an ionizer. An aerosol module injects finely divided droplets (such as water) into the gas stream; an ionizer injects electrical charge into the analyte molecules and/or the droplets. Alternatively, a SERS module can be used open to the atmosphere, or exposed to an aqueous environment such as a river, lake, sea, or precipitation.

Electrical bias may be applied to a SERS substrate to facilitate collection of charged species by electrostatic precipitation. Peltier cooling of the substrate may also be used to condense airborne species onto the substrate. Subsequently, programmed thermal desorption (volatilization) of the condensate may be used to fractionate the various chemical components in the condensate. Substrates may be chemically functionalized, for example using different thiols or other surface coatings.

Substrates may be contained in a hermetically sealed automatic dispensing cartridge. An improved sample cell may be integral with an autofocus objective lens, so that fresh substrates are dispensed at the focal plane. Gas flows across the substrate, and the first molecule to adsorb within the field of view is detected and identified by its Raman signature.

Single molecule detection can be achieved using microscope optics. Ensemble averaging of surface sites and of adsorbed molecules on substrates prepared according to the present invention limited the maximum SERS enhancement factor to around $10^7$-$10^8$. However, a Raman spectrometer operated near the single molecule limit can be used for single molecule detection.

Figure 17:
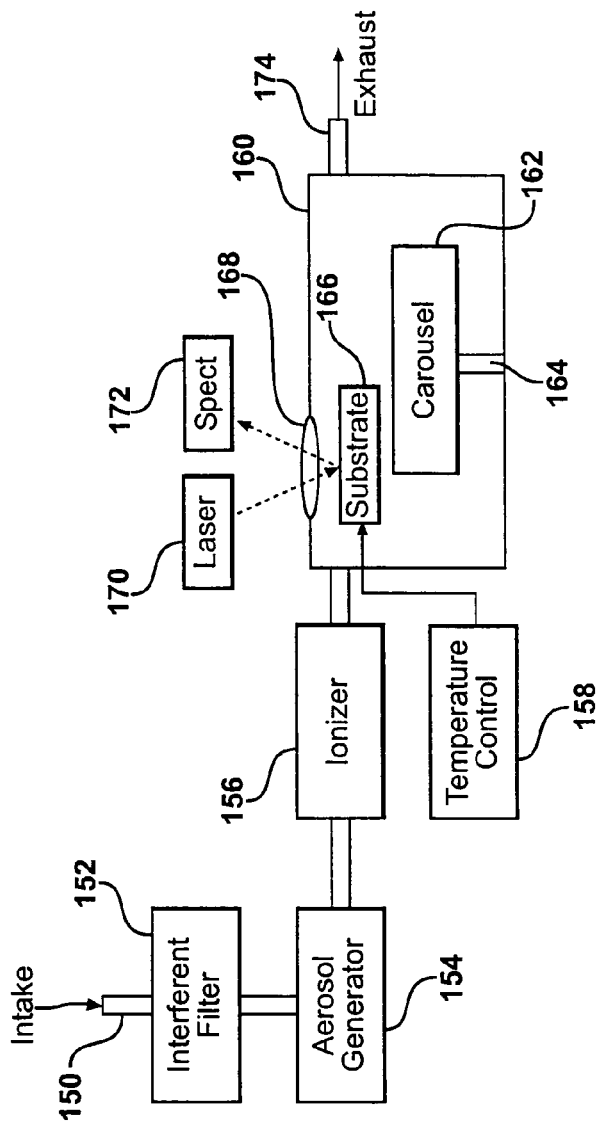
FIG. 17 shows a schematic of an example spectrometer configuration.

FIG. 17 shows a schematic of an example spectrometer configuration, comprising an inlet 150 through which the analyzed gas enters, an interferent filter 152, an aerosol generator 154, an ionizer 156, a housing 160 enclosing the substrate 166, a carousel 162 on spindle 164 for providing a replacement substrate at intervals, a laser 170, a spectrometer module 172, optics 168 for directing laser radiation to the substrate and for collecting scattered light and directing it to the spectrometer module, a temperature control 158, and an outlet 174. Raman spectrometers according to the present invention need not have all features described in this example. The spectrometer may be further operable to clean the substrate, for example using a UV source, ozone supply, gas jet, heating mechanism, and/or chemical applicator. The substrate may be removed from the path of the incindent radiation between cleaning. The substrate may be stored in an analyte-free chamber until required.

The temperature control can be used to cool the substrate to enhance absorption of the analyte on the substrate, and further to heat the substrate to drive off absorbed analytes, for example to allow re-use of the substrate. The temperature control may comprise an electrical heater and/or a Peltier cooler.

The laser can be a diode laser. The spectrometer module provides spectra from the received scattered light, and may, for example, comprise a dispersive element such as a grating or prism with a CCD array. The optics may comprise one or more windows and/or lenses in the housing. Additional optics may be associated with the laser and/or spectrometer module, which are not shown for illustrative clarity. Microscope optics may also be provided.

A carousel, cartridge, or other container can be used to isolate a substrate until it is needed, and then the substrate can be exposed to the flow of analyte gas through the housing. The carousel may support a number of wedge-shaped substrates that can be rotated sequentially into use. Substrates may be kept in a sealed container until needed. Substrates may be used once, then collected and removed from the spectrometer. Alternatively, the housing may further include a substrate cleaning feature. For example, substrates not being used may be subjected to heating and/or a flow of nitrogen or analyte-free air, UW, or ozone.

A spectrometer may comprise one or more laser sources, such as diode lasers at different, similar, or tunable wavelengths. A spectrometer may comprise a plurality of SERS substrates chosen for desired sensitivity to one or more analytes, as discussed in more detail below. A detector may detect Raman scattered radiation at a predetermined wavelength, for example using an optical filter, or by selecting a set of pixels on a CCD, so as to detect a predetermined analyte. Fiber optics can be used, allowing the laser and/or the detection optics to be remote from the substrate. For example, the substrate may be on the end of a wand or similar structure, and incident and scattered radiation conveyed through the wand by fiber optics.

For gold substrates, a laser wavelength of approximately 500 nm allows efficient coupling to surface plasmons within the substrate. A red laser, such as a diode laser or red HeNe laser, can be used. For silver substrates, green laser radiation couples well to surface plasmons. Hence, a green laser diode can be used with a silver substrate.

Improved substrates described herein can be used in sensors for monitoring air and water quality. Sensors can include holders for substrates (such as the porous metal films described herein) deployed in the relevant location to be monitored. After suitable time of exposure to the air, water, or other environment, substrates can be transferred into a Raman spectrometer for spectral collection. Substrates according to the present invention can be used with portable Raman spectrometers, e.g. for environmental testing.

Alternatively, adsorption can take place within a Raman spectrometer. The substrates can be provided in a sealed enclosure fitted with optics for the incoming and scattered laser light, and means to flow the air or water across the substrate within. A portable spectrometer may include a housing having a fluid inlet, a fluid outlet, a pump for conveying the fluid across a SERS substrate, and other conventional spectrometer components such as a laser, detector, and other optical components.

An improved Raman spectrometer can be specifically configured to accommodate a sealed substrate holder (or cell) and apparatus to pump the fluid to be tested through the cell. Substrates can be packaged in sealed housings prior to use, for example sealed under vacuum or under an inert atmosphere such as nitrogen.

Samples for analysis can be collected using a suction air flow sampler, gas syringe, liquid syringe, or other method. Samples may be collected from the atmosphere (exterior or within a building), from exhaled breath (for example, for health problem diagnosis), from water, or other source.

Detection of Target Analytes

SERS substrates formed using electrochemically roughened porous gold were used for rapid detection of target analytes. The limit of detection results for representative compounds was as follows: the explosive dinitro-toluene (DNT) was detected at 10 ppb; a toxic chemical surrogate dimethyl methyl phosphonate (DMMP) was detected at 100 ppb; methyl thio-uracil (MTU) was detected at 0.03 ppb; and dibromoquinolinol (DBQ) was detected at 0.12 ppb. Results correspond to a one minute exposure or less.

Substrate Cleaning and Re-Use

Compounds that are physically adsorbed on the substrate can be quickly removed using a flow of air or nitrogen over the substrate. Hence, in situ cleaning produces a substrate ready for re-use, and the same substrate may be used multiple times. Using a gentle stream of dry air impinging on a substrate previously exposed to DNT vapor, the substrates were cleaned within 10 to 15 minutes. Five exposure/cleaning cycles were carried out, and the spectra were similar with each cycle.

Compounds that chemically bind to the surface, such as thiols bonding to gold surfaces, may be removed using an electronic etching compound such as RCA-1. The properties of the substrate may change slightly (for example, a reduction of SERS intensity), but SERS enhancement of the same order of magnitude was observed. Substrates retain most of their SERS enhancement after cleaning away chemisorbed thiols using strong acids and peroxides, or using a UV/ozone cleaner.

UV/ozone treatment or RCA-1 oxidation for 15 to 45 minutes, plus rinsing with water, effectively removed thiols and reaction products, and possibly gold oxides. New SAMs were formed on these cleaned surfaces, and gave good SERS spectra, within an order of magnitude of the original intensity.

A SERS substrate may be placed remotely with automatic cleaning, and wireless control/signal outputs used to receive analytical data.

Molecular Sensitivity

SERS enhancements vary with molecular species and vibrational mode. It would be advantageous to have a sensor with preferential sensitivity to the particular compounds or classes of compounds being employed in an analytical application, especially since they must be detected at trace levels against an environmental background that may include higher concentrations of many other compounds. Furthermore, it is the nature of SERS to use small areas of substrate at any one time, so a field (portable) instrument can be made capable of simultaneously scanning a plurality of substrates having different SERS activity with respect to the pertinent ensemble of analytes and background compounds. SERS active substrates can be formed having preferential sensitivity to certain compounds or classes of compounds, for example through different surface treatments. The enhancement activity of a given SERS substrate toward certain compounds can be modified by coating it with another substance having different adsorption affinities with respect to those analytes.

Hence, a large number of analytes can be tracked independently with a single instrument. A highly sensitive and selective system can be configured for field use. Also, because Raman effect does not constrain the illumination source to certain particular frequencies, the excitation wavelength can be selected for engineering robustness, commercial availability, and affordability. Computer-aided analysis of SERS data, including the relative intensity of multiple Raman bands, can be used to reduce false positive detection of target analytes. The chemical specificity of a SERS substrate can be tailored by the choice of a SAM or other coating (such as a polymer or other chemical composition).

SERS substrates having a high density of Raman enhancing sites can be prepared using the described techniques. The product of the substrates' high site density and average site enhancement can substantially exceed that of other reported substrates. False positives and interferent effects can be reduced using ROC curves for SERS and multiple peak comparisons for a plurality of scattering peaks.

Other Applications

Films and patterned substrates prepared by a method according to the present invention may also be used as catalysts. For example, a porous gold film may be deposited on a titania substrate, or other substrate chosen to enhance the catalytic activity of the porous gold film.

Embodiments of the present invention combine more than one process to create SERS substrates having desired characteristics. In one example, a patterned gold substrate is first prepared by a non-electrochemical method, and then used as the electrode in a second, electrochemical process. The resulting SERS substrates have enhancement factors that are many times greater than result from either of the two processes independently. To the best of our knowledge, there is no previous report in which a porous gold process is used for preparing SERS substrates.

Patents, patent applications, or publications mentioned in this specification are incorporated herein by reference to the same extent as if each individual document was specifically and individually indicated to be incorporated by reference. In particular, U.S. Prov. Pat. App. Ser. No. 60/612,291, filed Sep. 22, 2004, is incorporated herein in its entirety.

The invention is not restricted to the illustrative examples described above. Examples are not intended as limitations on the scope of the invention. Methods, apparatus, compositions, and the like described herein are exemplary and not intended as limitations on the scope of the invention. Changes therein and other uses will occur to those skilled in the art. The scope of the invention is defined by the scope of the claims.

We claim:

1. A method of preparing a substrate for surface enhanced Raman spectroscopy, the method comprising:
    preparing an alloy film, the alloy film including a first metal and a second metal; and
    removing most of the second metal, so as to obtain a porous film of the first metal, the porous film of the first metal being the substrate for surface enhanced Raman spectroscopy.

2. The method of claim 1, wherein removing most of the second metal comprises acid etching of the alloy film, the acid dissolving the second metal.

3. The method of claim 1, wherein preparing the alloy film comprises sputter deposition of the alloy film.

4. The method of claim 1, wherein the first metal is gold.

5. The method of claim 4, wherein the second metal is silver.

6. The method of claim 1, wherein the alloy film has a film thickness, the film thickness being less than approximately 500 nm.

7. The method of claim 5, wherein the film thickness is between approximately 150 nm and approximately 500 nm.

8. The method of claim 1, wherein removing most of the second metal comprises acid etching of the second metal from the alloy film.

9. The method of claim 1, further comprising electrochemical roughening of the porous film of the first metal.

10. A substrate useful for surface enhanced Raman spectroscopy (SERS), the substrate comprising a porous metal film,
    the porous metal film having a film thickness between approximately 150 nm and approximately 500 nm, and
    the substrate having a SERS enhancement factor of at least $10^7$.

11. The substrate of claim 10, wherein the porous metal film has a columnar structure.

12. The substrate of claim 10, wherein the porous metal film includes a metal selected from a group of metals consisting of gold, silver, and platinum.

13. An apparatus for detecting an analyte, comprising:
    a substrate;
    a radiation source, the radiation source operable to provide incident radiation on the substrate; and
    a detector, the detector positioned to receive scattered radiation from the analyte when the analyte is adsorbed on the substrate, the scattered radiation being used to detect the analyte,
    wherein the substrate comprises the porous metal film of claim 10,
    the porous metal film including a metal selected from a group of metals consisting of gold, platinum, and silver.

14. The apparatus of claim 13, wherein the incident radiation has a wavelength that excites surface plasmons within the substrate.

15. The apparatus of claim 13, wherein the substrate is a porous gold film.

16. The apparatus of claim 13, wherein the substrate is an electrochemically roughened porous gold film.

17. The apparatus of claim 13, wherein the porous metal film has a film thickness between approximately 150 nm and approximately 500 nm.

18. The apparatus of claim 13, the apparatus further operable to clean the substrate so as to remove the analyte from the substrate.

19. The apparatus of claim 13, wherein the apparatus is a Raman spectrometer, and the radiation source is a laser.

20. The apparatus of claim 13, wherein the substrate is supported on a rotating carousel, the rotating carousel supporting a plurality of substrates.

* * * * *

UNITED STATES PATENT AND TRADEMARK OFFICE
CERTIFICATE OF CORRECTION

PATENT NO.         : 7,450,227 B2                                   Page 1 of 1
APPLICATION NO.    : 11/231177
DATED              : November 11, 2008
INVENTOR(S)        : David W. Dwight et al.

It is certified that error appears in the above-identified patent and that said Letters Patent is hereby corrected as shown below:

Column 11, line 38, replace "WV" with --UV--

Column 13, line 31, replace "Skokie, ILL" with --Skokie, IL--

Column 13, line 34, replace "I1Ia" with --IIIa--

Column 15, line 35, replace "UW" with --UV--

Signed and Sealed this

Twenty-fourth Day of March, 2009

JOHN DOLL
*Acting Director of the United States Patent and Trademark Office*